US00PP17762P3

(12) United States Plant Patent
Arita

(10) Patent No.: US PP17,762 P3
(45) Date of Patent: May 29, 2007

(54) *COLEUS* PLANT NAMED 'KAKEGAWA CE11'

(50) Latin Name: *Solenostemon scutellarioides*
Varietal Denomination: Kakegawa CE11

(75) Inventor: Yo Arita, San Jose (CR)

(73) Assignee: Sakata Seed Corporation, Yokohama (JP)

( * ) Notice: Subject to any disclaimer, the term of this patent is extended or adjusted under 35 U.S.C. 154(b) by 340 days.

(21) Appl. No.: 11/067,979

(22) Filed: Feb. 28, 2005

(65) Prior Publication Data

US 2006/0195961 P1 Aug. 31, 2006

(51) Int. Cl.
*A01H 5/00* (2006.01)

(52) U.S. Cl. ..... Plt./373

(58) Field of Classification Search ..... Plt./373
See application file for complete search history.

*Primary Examiner*—Kent Bell
(74) *Attorney, Agent, or Firm*—Jondle & Associates P.C.

(57) ABSTRACT

'Kakegawa CE11' is a new *Coleus* cultivar particularly distinguished by having a unique leaf shape and color.

1 Drawing Sheet

Genus and species: *Solenostemon scutellarioides*.
Variety denomination: 'Kakegawa CE11'.

BACKGROUND OF THE INVENTION

The present invention comprises a new and distinct cultivar of *Coleus*, botanically known as *Solenostemon scutellarioides* and hereinafter referred to by the cultivar name 'Kakegawa CE11'. It is characterized by having a unique leaf shape and color. The new cultivar originated as a selection from a population resulting from self-pollination of a proprietary *Coleus* breeding line. $S_1$ seed was sown in a greenhouse in Cartago, Costa Rica. Four single-plant selections were made from the $S_1$ generation and self-pollinated to create four separate $S_2$ seed lots. $S_2$ seed from each lot was sown in a greenhouse and later transplanted into 16 cm diameter pots. One single-plant selection was made from the $S_2$ plants based on its rose with green edge leaf color and unique leaf shape. In 2002, this selection was asexually propagated through rooted plant cuttings in Salinas, Calif. 'Kakegawa CE11' has been shown to reproduce true to type in successive generations of asexual propagation.

DESCRIPTION OF PHOTOGRAPHS

This new *Coleus* plant is illustrated by the accompanying photographs which show the plant's form and foliage. The colors shown are as true as can be reasonably obtained by conventional photographic procedures.

Figure 1:
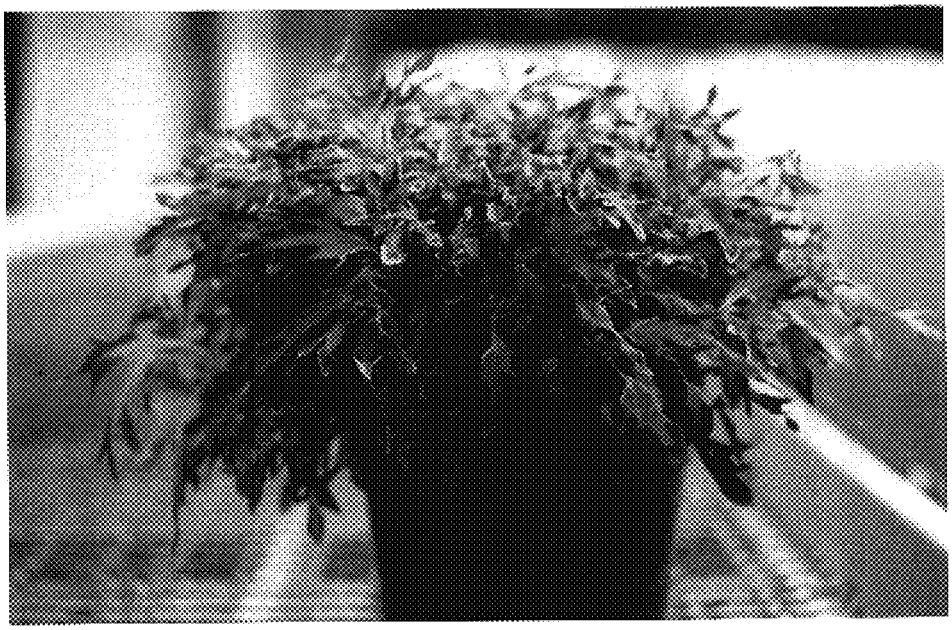

FIG. 1. shows overall plant habit.

Figure 2:
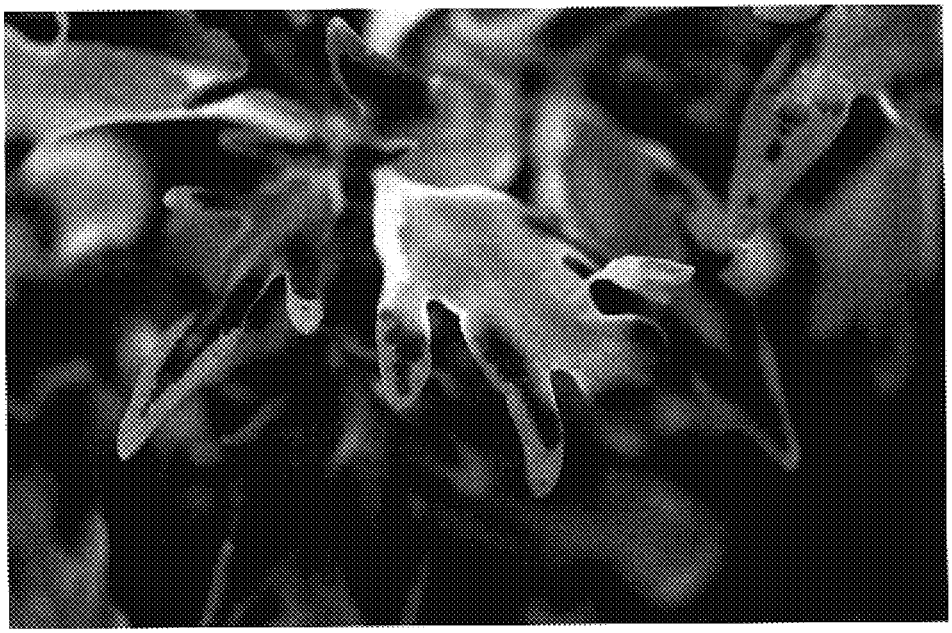

FIG. 2. shows a close-up view of the leaves.

DESCRIPTION OF THE NEW CULTIVAR

The following detailed description sets forth the distinctive characteristics of 'Kakegawa CE11'. The data which define these characteristics were collected from asexual reproductions carried out in Salinas, Calif. The detailed description was taken from plants grown under greenhouse conditions for approximately 4 months from transplanting of rooted cuttings. Color references are to The R.H.S. Colour Chart of The Royal Horticultural Society of London (R.H.S.), 4$^{th}$ Edition.

DETAILED BOTANICAL DESCRIPTION

Classification:
- *Family.*—Lamiaceae Lindl.
- *Species.*—*Solenostemon scutellarioides* cultivar 'Kakegawa CE11'.
- *Common name.*—*Coleus.*

Parentage:
- *Male.*—Proprietary *Coleus* breeding line.
- *Female.*—Proprietary *Coleus* breeding line.

Plant description:
- *Form.*—Mounding.
- *Habit.*—Heavily branching.
- *Height.*—About 14 cm as measured from soil level to top of plant.
- *Spread.*—About 35 cm.

Propagation:
- *Type cuttings.*—Vegetative cuttings.
- *Time to produce a rooted cutting.*—5–6 weeks.

Environmental conditions for plant growth: The terminal 1.0–1.5 inches of actively growing stems were excised and the base of each cutting dipped for one to two seconds in a 1:9 solution of DIP 'N GROW root inducing solution immediately prior to placing the cutting into a cell tray. The cell tray contained a moistened peat moss-based growing medium. The cuttings were misted with water from overhead for 10 seconds every 30 minutes until sufficient roots were formed. Rooted cuttings were transplanted and grown individually in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow-release fertilizer containing 20% nitrogen, 10% phosphorous and 18% potassium. The typical average air temperature was 24° C. 'Kakegawa CE11' will tolerate a wide range of temperatures, from 2° C. to 35° C.

Lateral branches:

*Branch color.*—RHS 143B (yellow-green).
*Texture.*—Pubescent.
*Pubescence color.*—N155A (white).
*Stem description.*—Ancipital (round) in cross-section.
*Branch diameter.*—0.5 cm.
*Branch length.*—15.0–20.0 cm.
*Internode length.*—2.0–2.5 cm.
*Aspect.*—Upright.

Leaves:

*Leaf arrangement.*—Opposite.
*Leaf size.*—Developing leaves: Length: 3.0–3.5 cm. Width: 1.5–2.0 cm. Mature leaves: Length: 5.0–6.5 cm. Width: 2.5–3.0 cm.
*Leaf shape.*—Parted; developing leaves have 3 lobes, mature leaves have 4 lobes.
*Leaf apex.*—Mucronate (each lobe).
*Leaf base.*—Decurrent.
*Leaf margin.*—Entire (each lobe).
*Leaf texture, both surfaces.*—Sparsely pubescent.
*Pubescence color.*—N155A (white).
*Venation.*—Pinnate.
*Leaf color* (*multicoloured; colors arranged in bands starting at leaf base and moving outwardly toward leaf edge*).—Developing foliage: Upper surface: base is RHS 57D (red-purple); middle band is RHS 147A (yellow-green); edge is RHS 143A (green) Lower surface: base is RHS 182D (gray-red); edge is RHS 137D (green); midvein is RHS 2C (yellow). Fully expanded foliage: Upper surface: base is RHS 61C (red-purple); inner band is RHS 23B (yellow-orange); outer band is RHS 147A (yellow-green); edge is RHS 141B (green). Lower surface: base is RHS 182D (gray-red); edge is RHS 137C (green); midvein is RHS 2C (yellow).
*Petiole length.*—1.0–1.5 cm.
*Petiole diameter.*—0.1–0.2 cm.
*Petiole color.*—RHS 2C (yellow).

Disease and Insect Resistance

'Kakegawa CE11' has no unique resistance or susceptibility to common *Coleus* pathogens or pests.

Comparison with Known Cultivars

*Coleus* 'Kakegawa CE11' is a distinct variety of *Coleus* due to its unique leaf shape and color. 'Kakegawa CE11' is distinguished from Breeding Line 2WC mainly by its leaf color as shown in Table 1 below.

TABLE 1

| Characteristic | 'Kakegawa CE11' | Breeding Line 2WC |
|---|---|---|
| Leaf color, upper surface | Multicolor; base is RHS 61C (red-purple); inner band is RHS 23B (yellow-orange); outer band is RHS 147A (yellow-green); edge is RHS 141B (green); color brighter than breeding line 2WC; contrast between center and edge greater than breeding line 2WC | Multicolor; light red center with green edge |

'Kakegawa CE11' is most similar to the *Coleus* variety 'Trailing Salamander' (Unpatented); however, there are differences in leaf color and growth habit as described in Table 2 below.

'Kakegawa CE11' is distinguished from its parental cultivars primarily in foliage coloration.

TABLE 2

| Characteristic | 'Kakegawa CE11' | 'Trailing Salamander' |
|---|---|---|
| Leaf color | Multicolor; Upper (from base to edge): red-purple, yellow-orange, dark green, green | Bi-color; Upper central: black, solid. Upper edge: green |
| Leaf shape | Parted/multi-lobed | Ovate to deltoid |

I claim:

1. A new and distinct cultivar of *Coleus* plant as shown and described herein.

* * * * *